US011589607B2

(12) United States Patent
Capelli et al.

(10) Patent No.: US 11,589,607 B2
(45) Date of Patent: Feb. 28, 2023

(54) NICOTINE GEL

(71) Applicant: Philip Morris Products S.A., Neuchatel (CH)

(72) Inventors: Sebastien Capelli, Neuchatel (CH); Celine Gambs, Neuchatel (CH); Farideh Goudarzi, Cambridge (GB); Timothy King, Cambridge (GB); Jean-Yves Vollmer, Neuchatel (CH); Gerard Zuber, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 118 days.

(21) Appl. No.: 17/040,284

(22) PCT Filed: Apr. 8, 2019

(86) PCT No.: PCT/EP2019/058849
§ 371 (c)(1),
(2) Date: Sep. 22, 2020

(87) PCT Pub. No.: WO2019/193209
PCT Pub. Date: Oct. 10, 2019

(65) Prior Publication Data
US 2021/0085666 A1    Mar. 25, 2021

(30) Foreign Application Priority Data
Apr. 6, 2018 (EP) ..................... 18166166

(51) Int. Cl.
| | | |
|---|---|---|
| A24B 15/167 | (2020.01) |
| A24B 15/32 | (2006.01) |
| A24B 15/40 | (2006.01) |
| A61K 9/06 | (2006.01) |
| A61K 31/465 | (2006.01) |
| A61K 47/10 | (2017.01) |
| A61K 47/36 | (2006.01) |
| A61K 9/00 | (2006.01) |
| A61K 36/185 | (2006.01) |
| A61K 47/02 | (2006.01) |
| A61K 47/12 | (2006.01) |
| A61K 47/46 | (2006.01) |

(52) U.S. Cl.
CPC ............ *A24B 15/167* (2016.11); *A24B 15/32* (2013.01); *A24B 15/403* (2013.01); *A61K 9/007* (2013.01); *A61K 9/06* (2013.01); *A61K 31/465* (2013.01); *A61K 36/185* (2013.01); *A61K 47/02* (2013.01); *A61K 47/10* (2013.01); *A61K 47/12* (2013.01); *A61K 47/36* (2013.01); *A61K 47/46* (2013.01)

(58) Field of Classification Search
CPC ..... A24B 15/167; A24B 15/32; A24B 15/403; A24B 15/302; A24B 15/243; A61K 9/007; A61K 9/06; A61K 31/465; A61K 36/185; A61K 47/02; A61K 47/10; A61K 47/12; A61K 47/36; A61K 47/46
See application file for complete search history.

(56) References Cited

U.S. PATENT DOCUMENTS

| | | | |
|---|---|---|---|
| 4,746,528 A | 5/1988 | Prest et al. | |
| 6,080,783 A | 6/2000 | Davidson et al. | |
| 6,365,624 B1 | 4/2002 | Davidson et al. | |
| 6,673,835 B1 | 1/2004 | Hensley et al. | |
| 2002/0032231 A1 | 3/2002 | Davidson et al. | |
| 2004/0109895 A1 | 6/2004 | Hensley et al. | |
| 2005/0118243 A1 | 6/2005 | Hensley et al. | |
| 2007/0265337 A1 | 11/2007 | Hensley et al. | |
| 2007/0269386 A1* | 11/2007 | Steen ........................ A61P 1/00 424/440 |
| 2010/0063110 A1 | 3/2010 | Meyer et al. | |
| 2011/0077296 A1 | 3/2011 | Hensley et al. | |
| 2016/0120225 A1* | 5/2016 | Mishra .................... A24F 40/46 392/386 |
| 2018/0029782 A1 | 2/2018 | Zuber et al. | |

FOREIGN PATENT DOCUMENTS

| | | |
|---|---|---|
| CN | 101933653 B | 10/2012 |
| CN | 103960783 A | 8/2014 |
| CN | 103960784 A | 8/2014 |
| CN | 104382236 A | 3/2015 |
| CN | 104770858 A | 7/2015 |
| CN | 104256888 B | 6/2016 |
| CN | 105768201 A | 7/2016 |
| CN | 106998811 A | 8/2017 |
| CN | 107126411 A | 9/2017 |
| WO | WO 00/12081 A1 | 3/2000 |
| WO | WO 2008/112124 A2 | 9/2008 |
| WO | WO 2014/126985 A1 | 8/2014 |

(Continued)

OTHER PUBLICATIONS

Masakuni Tako, "The Principle of Polysaccharide Gels" Advances in Bioscience and Biotechnology, vol. 6, 2015, pp. 22-36.
International Search Report and Written Opinion dated Jul. 4, 2019 in PCT/EP2019/058849 filed Apr. 8, 2019.
Combined Chinese Office Action and Search Report dated Jun. 22, 2022, in corresponding Chinese Patent Application No. 2019800198530 (with English Translation), 18 pages.

(Continued)

*Primary Examiner* — Robert A Wax
*Assistant Examiner* — Quanglong N Truong
(74) *Attorney, Agent, or Firm* — Oblon, McClelland, Maier & Neustadt, L.L.P.

(57) ABSTRACT

A gel composition is provided, including an alkaloid compound, or a cannabinoid compound, or both an alkaloid compound and a cannabinoid compound; glycerol; a viscosifying agent; a hydrogen-bond crosslinking gelling agent; and an ionic crosslinking gelling agent; and an acid.

16 Claims, 2 Drawing Sheets

(56) References Cited

FOREIGN PATENT DOCUMENTS

| | | |
|---|---|---|
| WO | WO 2016/069876 A1 | 5/2016 |
| WO | WO 2016/069903 A1 | 5/2016 |
| WO | WO 2016/133109 A1 | 8/2016 |
| WO | WO 2018/019543 A1 | 2/2018 |
| WO | WO 2019/129470 A1 | 7/2019 |

OTHER PUBLICATIONS

Combined Chinese Office Action and Search Report dated Jan. 19, 2022 in Patent Application No. 2019800198530 (with English language translation), 17 pages.

* cited by examiner

NICOTINE GEL

This disclosure relates to an alkaloid or cannabinoid gel that may be utilized with an aerosol-generating device. In some aspects this disclosure relates to nicotine gel that may be utilized with an aerosol-generating device.

Nicotine compositions for use with aerosol-generating articles are known. Often the nicotine composition is a liquid composition, such as an e-liquid, that is heated by a coiled electrically resistive filament of an aerosol-generating article. To avoid accidental leakage of the liquid composition, a good deal of care is taken to manufacture the containers holding this liquid composition. Accidental leakage may, in particular, occur when the container is made of paper, cardboard or any material that could absorb or could be damaged by a liquid nicotine composition.

Use of alternative forms of compositions comprising nicotine may reduce potential leakage concerns. However, these alternative forms of compositions comprising nicotine may change phase from gel to liquid over time. In particular, gel forms of compositions comprising nicotine may release a liquid phase upon storage or from manufacture to consumption by the user. This is particularly true for gel compositions comprising a high level of glycerol, a low level of water, or both a high level of glycerol and a low level of water.

It would be desirable to provide a gel composition comprising an alkaloid compound, such as nicotine, or a cannabinoid compound, such as cannabidiol or tetrahydrocannabinol, with improved physical stability. It would be desirable to provide a gel composition comprising an alkaloid compound, such as nicotine, or a cannabinoid compound, such as cannabidiol or tetrahydrocannabinol, that may be physically stable. It would be desirable to provide a gel composition comprising an alkaloid compound, such as nicotine, or a cannabinoid compound, such as cannabidiol or tetrahydrocannabinol, that did not release liquid phase over a broad range of storage conditions. It would be desirable to provide a gel composition comprising an alkaloid compound, such as nicotine, or a cannabinoid compound, such as cannabidiol or tetrahydrocannabinol, that did not absorb liquid phase. It would be desirable to provide a gel phase composition that vaporizes an alkaloid compound, such as nicotine, or a cannabinoid compound, such as cannabidiol or tetrahydrocannabinol, within the composition upon heating. It would be desirable to provide a gel composition comprising an alkaloid compound, such as nicotine, or a cannabinoid compound, such as cannabidiol or tetrahydrocannabinol, that did not leak out of an aerosol-generating device.

Various aspects of the disclosure relate to gel compositions that include an alkaloid compound, or a cannabinoid compound, or both an alkaloid compound and a cannabinoid compound. Various aspects of the disclosure relate to gel compositions that include nicotine. These gel compositions may not release or absorb water over a broad range of relative humidifies (such as from about 10% to about 60% relative humidity, for example). The gel composition includes: an alkaloid compound, or a cannabinoid compound, or both an alkaloid compound and a cannabinoid compound; glycerol; a hydrogen-bond crosslinking gelling agent; an ionic crosslinking gelling agent; a viscosifying agent; and an acid.

The gel composition may include: an alkaloid compound, or a cannabinoid compound, or both an alkaloid compound and a cannabinoid compound; at least about 50% wt. glycerol or at least 70% wt. glycerol; at least about 0.2% wt. hydrogen-bond crosslinking gelling agent; at least about 0.2% wt. ionic crosslinking gelling agent; at least about 0.2% wt. viscosifying agent; and an acid.

The gel composition may include nicotine, at least about 50% wt. glycerol or at least 70% wt. glycerol, at least about 0.2% wt. hydrogen-bond crosslinking gelling agent, at least about 0.2% wt. ionic crosslinking gelling agent, at least about 0.2% wt. viscosifying agent, and an acid.

The gel composition may include the viscosifying agent, hydrogen-bond crosslinking gelling agent, and ionic crosslinking gelling agent in a total amount from about 1% wt. to about 8% wt.

The gel composition may include from about 0.5% wt. to about 2% wt. of viscosifying agent. The gel composition may include from about 0.5% wt. to about 2% wt. of hydrogen-bond crosslinking gelling agent. The gel composition may include from about 0.5% wt. to about 2% wt. of ionic crosslinking gelling agent. The gel composition may include from about 0.5% wt. to about 2% wt. of the viscosifying agent, from about 0.5% wt. to about 2% wt. of the hydrogen-bond crosslinking gelling agent, and from about 0.5% wt. to about 2% wt. of the ionic crosslinking gelling agent. Each of the viscosifying agent, hydrogen-bond crosslinking gelling agent, and ionic crosslinking gelling agent may be present in the gel composition in substantially equal amounts by weight.

The gel composition may include: about 0.5% to 2.5% wt. of an alkaloid compound, or about 0.5% to 2.5% wt. of a cannabinoid compound, or both an alkaloid compound and a cannabinoid compound in a total amount from about 0.5% to 2.5% wt.; about 70% to 80% wt. glycerol; about 0.5% to 2% wt. hydrogen-bond crosslinking gelling agent; about 0.5% to 2% wt. ionic crosslinking gelling agent; about 0.5% to 2% wt. viscosifying agent; about 15% to about 25% wt. water; divalent cations; and an acid. Each of the viscosifying agent, hydrogen-bond crosslinking gelling agent, and ionic crosslinking gelling agent may be present in the gel composition in substantially equal amounts by weight.

The gel composition may include: about 0.5% to 2.5% wt. nicotine; about 70% to 80% wt. glycerol; about 0.5% to 2% wt. hydrogen-bond crosslinking gelling agent; about 0.5% to 2% wt. ionic crosslinking gelling agent; about 0.5% to 2% wt. viscosifying agent; about 15 to about 25% wt. water; divalent cations; and an acid. Each of the viscosifying agent, hydrogen-bond crosslinking gelling agent, and ionic crosslinking gelling agent may be present in the gel composition in substantially equal amounts by weight.

The gel composition may include: about 1.5% to 2.5% wt. of an alkaloid compound, or about 1.5% to 2.5% wt. of a cannabinoid compound, or both an alkaloid compound and a cannabinoid compound in a total amount from about 1.5% to 2.5% wt.; about 70% to about 75% wt. glycerol; about 18% to about 22% wt. water; about 0.5% to about 2% wt. each of agar, xanthan gum and low acyl gellan; calcium ions; and a carboxylic acid such as lactic acid. Each of the xanthan gum, agar, and low acyl gellan may be present in the gel composition in substantially equal amounts by weight.

The gel composition may include: about 1.5% to about 2.5% wt. nicotine; about 70% to about 75% wt. glycerol; about 18% to about 22% wt. water; about 0.5% to about 2% wt. each of agar, xanthan gum and low acyl gellan; calcium ions; and a carboxylic acid such as lactic acid. Each of the xanthan gum, agar, and low acyl gellan may be present in the gel composition in substantially equal amounts by weight.

The gel composition may include a gelling agent forming a solid medium, glycerol dispersed in the solid medium, and an alkaloid compound, or a cannabinoid compound, or both an alkaloid compound and a cannabinoid compound dispersed in the glycerol. The composition forming a stable gel phase.

The gel composition may include a gelling agent forming a solid medium, glycerol dispersed in the solid medium, and nicotine dispersed in the glycerol. The composition forming a stable gel phase.

The gel composition may include at least two gelling agents forming a solid medium, glycerol dispersed in the solid medium, and an alkaloid compound, or a cannabinoid compound, or both an alkaloid compound and a cannabinoid compound dispersed in the glycerol. The composition forming a stable gel phase.

The gel composition may include at least two gelling agents forming a solid medium, glycerol dispersed in the solid medium, and nicotine dispersed in the glycerol. The composition forming a stable gel phase.

The gel composition may include a viscosifying agent, and gelling agent forming a solid medium, glycerol dispersed in the solid medium, and an alkaloid compound, or a cannabinoid compound, or both an alkaloid compound and a cannabinoid compound dispersed in the glycerol. The composition forming a stable gel phase.

The gel composition may include a viscosifying agent, and gelling agent forming a solid medium, glycerol dispersed in the solid medium, and nicotine dispersed in the glycerol. The composition forming a stable gel phase.

The gel composition may include a viscosifying agent, and at least two gelling agents forming a solid medium, glycerol dispersed in the solid medium, and an alkaloid compound, or a cannabinoid compound, or both an alkaloid compound and a cannabinoid compound dispersed in the glycerol. The composition forming a stable gel phase.

The gel composition may include a viscosifying agent, and at least two gelling agents forming a solid medium, glycerol dispersed in the solid medium, and nicotine dispersed in the glycerol. The composition forming a stable gel phase.

Further aspects of the disclosure may relate to the use of the composition by heating the composition to vaporize an alkaloid compound, or a cannabinoid compound, or both an alkaloid compound and a cannabinoid compound, and the use of the composition wherein the heating does not release a liquid phase from the composition.

Further aspects of the disclosure may relate to the use of the composition by heating the composition to vaporize nicotine, and the use of the composition wherein the heating does not release a liquid phase from the composition.

Advantageously the gel is solid at room temperature. "Solid" in this context means that the gel has a stable size and shape and does not flow. Room temperature in this context means 25 degrees Celsius. A gel may be defined as a substantially dilute cross-linked system, which exhibits no flow when in the steady-state. By weight, gels may be mostly liquid, yet they behave like solids due to a three-dimensional cross-linked network within the liquid. It is the crosslinking within the fluid that gives a gel its structure (hardness). In this way gels may be a dispersion of molecules of a liquid within a solid in which liquid particles are dispersed in the solid medium.

Preferably the gel composition has a viscosity of about 1,000,000 to about 1 Pascal per second, preferably 100,000 to 10 Pascal per second, preferably 10,000 to 1,000 Pascal per second, or 1,000 to 100 Pascal per second, or 500 to 200 Pascal per second to give the desired viscosity. Viscosity of the gel composition can be measured by taking the viscosity of a sample using an Anton Paar MCR 302 rheometer using a parallel plate PP25 with a P-PTD200+H-PTD200 measuring cell at 25° C. at a shear rate of 1 $s^{-1}$.

The gel composition's mass may not change by more than about 20%, or may not change by more than about 15%, or may not change by more than about 10%, when exposed to a variety of environmental storage conditions. The composition may have an exterior shape with an exposed surface area that does not change by more than about 10%, or does not change by more than about 5%, or does not change by more than about 1%, when exposed to a variety of environmental conditions.

In one or more aspects, the gel composition has a mass and the mass does not change by more than about 20%, or does not change by more than about 15%, or does not change by more than about 10%, when exposed to a relative humidity in a range from about 10% to about 60% at 24 degrees Celsius and one atmosphere, or typical storage conditions.

In one or more aspects, the gel composition has an exterior shape with an exposed surface area that does not change by more than about 10%, or does not change by more than about 5%, or does not change by more than about 1%, when exposed to a relative humidity in a range from about 10% to about 60% at 24 degrees Celsius and one atmosphere In one or more aspects, the gel composition has an exposed surface area value (in $m^2$) and a mass value (in kg), the mass value to exposed surface area value is in a range from about 0.05:1 to about 1:1, or from about 0.1:1 to about 1:1, or from about 0.5:1 to about 1:0.1, or from about 0.5:1 to about 1:0.5.

Advantageously, a gel composition provides predictable composition form upon storage or transit from manufacture to the consumer. The gel composition comprising an alkaloid compound, or a cannabinoid compound, or both an alkaloid compound and a cannabinoid compound substantially maintains its shape. The gel composition comprising an alkaloid compound, or a cannabinoid compound, or both an alkaloid compound and a cannabinoid compound substantially does not release a liquid phase upon storage or transit from manufacture to the consumer. The gel composition comprising nicotine substantially maintains its shape. The gel composition comprising nicotine substantially does not release a liquid phase upon storage or transit from manufacture to the consumer. The gel composition may provide for a simple consumable design. This consumable may not have to be designed to contain a liquid, thus a wider range of materials and container constructions may be contemplated.

The gel composition described herein may be combined with an aerosol-generating device to provide an alkaloid compound aerosol to the lungs at inhalation or air flow rates that are within conventional smoking regime inhalation or air flow rates. The aerosol-generating device may continuously heat the gel composition. A consumer may take a plurality of inhalations or "puffs" where each "puff" delivers an amount of alkaloid compound aerosol. The gel composition may be capable of delivering a high alkaloid compound/low total particulate matter (TPM) aerosol to a consumer when heated, preferably in a continuous manner.

The gel composition described herein may be combined with an aerosol-generating device to provide a nicotine aerosol to the lungs at inhalation or air flow rates that are within conventional smoking regime inhalation or air flow rates. The aerosol-generating device may continuously heat the gel composition. A consumer may take a plurality of inhalations or "puffs" where each "puff" delivers an amount of nicotine aerosol. The gel composition may be capable of delivering a high nicotine/low total particulate matter (TPM) aerosol to a consumer when heated, preferably in a continuous manner.

The gel composition described herein may be combined with an aerosol-generating device to provide a cannabinoid compound aerosol to the lungs at inhalation or air flow rates that are within conventional smoking regime inhalation or air flow rates. The aerosol-generating device may continuously heat the gel composition. A consumer may take a plurality of inhalations or "puffs" where each "puff" delivers an amount of cannabinoid compound aerosol. The gel composition may be capable of delivering a high cannabinoid compound/low total particulate matter (TPM) aerosol to a consumer when heated, preferably in a continuous manner.

The gel composition includes an alkaloid compound, or a cannabinoid compound, or both an alkaloid compound and a cannabinoid compound. The gel composition may include one or more alkaloids. The gel composition may include one or more cannabinoids. The gel composition may include a combination of one or more alkaloids and one or more cannabinoids.

The term "alkaloid compound" refers to any one of a class of naturally occurring organic compounds that contain one or more basic nitrogen atoms. Generally, an alkaloid contains at least one nitrogen atom in an amine-type structure. This or another nitrogen atom in the molecule of the alkaloid compound can be active as a base in acid-base reactions. Most alkaloid compounds have one or more of their nitrogen atoms as part of a cyclic system, such as for example a heterocylic ring. In nature, alkaloid compounds are found primarily in plants, and are especially common in certain families of flowering plants. However, some alkaloid compounds are found in animal species and fungi. In this disclosure, the term "alkaloid compound" refers to both naturally derived alkaloid compounds and synthetically manufactured alkaloid compounds.

The gel composition may preferably include an alkaloid compound selected from the group consisting of nicotine, anatabine, and combinations thereof.

Preferably the gel composition includes nicotine.

The term "nicotine" refers to nicotine and nicotine derivatives such as free-base nicotine, nicotine salts and the like.

The term "cannabinoid compound" refers to any one of a class of naturally occurring compounds that are found in parts of the *cannabis* plant—namely the species *Cannabis sativa, Cannabis indica*, and *Cannabis ruderalis*. Cannabinoid compounds are especially concentrated in the female flower heads. Cannabinoid compounds naturally occurring in the *cannabis* plant include cannabidiol (CBD) and tetrahydrocannabinol (THC). In this disclosure, the term "cannabinoid compounds" is used to describe both naturally derived cannabinoid compounds and synthetically manufactured cannabinoid compounds.

The gel may include a cannabinoid compound selected from the group consisting of cannabidiol (CBD), tetrahydrocannabinol (THC), tetrahydrocannabinolic acid (THCA), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), and combinations thereof.

The gel composition may preferably include a cannabinoid compound selected from the group consisting of cannabidiol (CBD), THC (tetrahydrocannabinol) and combinations thereof.

The gel may preferably include cannabidiol (CBD).

The gel composition may include nicotine and cannabidiol (CBD).

The gel composition may include nicotine, cannabidiol (CBD), and THC (tetrahydrocannabinol).

The phrase "stable gel phase" or "stable gel" refers to gel that substantially maintains its shape and mass when exposed to a variety of environmental conditions. The stable gel may not substantially release (sweat) or absorb water when exposed to a standard temperature and pressure while varying relative humidity from about 10% to about 60%. For example, the stable gel may substantially maintain its shape and mass when exposed to a standard temperature and pressure while varying relative humidity from about 10% to about 60%.

The term "viscosifying agent" refers to a compound that, when added homogeneously into a 25° C., 50% wt. water/50% wt. glycerol mixture, in an amount of 0.3% wt., increases the viscosity without leading to the formation of a gel, the mixture staying or remaining fluid. Preferably the viscosifying agent refers to a compound that when added homogeneously into a 25° C. 50% wt. water/50% wt. glycerol mixture, in an amount of 0.3% wt., increases the viscosity to at least 50 cPs, preferably at least 200 cPs, preferably at least 500 cPs, preferably at least 1000 cPs at a shear rate of 0.1 s$^{-1}$, without leading to the formation of a gel, the mixture staying or remaining fluid. Preferably the viscosifying agent refers to a compound that when added homogeneously into a 25° C. 50% wt. water/50% wt. glycerol mixture, in an amount of 0.3% wt., increases the viscosity at least 2 times, or at least 5 times, or at least 10 times, or at least 100 times higher than before addition, at a shear rate of 0.1 s$^{-1}$, without leading to the formation of a gel, the mixture staying or remaining fluid.

The viscosity values recited herein can be measured using a Brookfield RVT viscometer rotating a disc type RV #2 spindle at 25° C. at a speed of 6 revolutions per minute (rpm).

The term "gelling agent" refers to a compound that homogeneously, when added to a 50% wt. water/50% wt. glycerol mixture, in an amount of about 0.3% wt., forms a solid medium or support matrix leading to a gel. Gelling agents include, but are not limited to, hydrogen-bond crosslinking gelling agents, and ionic crosslinking gelling agents.

The term "gel" refers to a solid at room temperature. "Solid" in this context means that the gel has a stable size and shape and does not flow. Room temperature in this context means 25 degrees Celsius. A gel may be defined as a substantially dilute cross-linked system, which exhibits no flow when in the steady-state. By weight, gels may be mostly liquid, yet they behave like solids due to a three-dimensional cross-linked network within the liquid. It is the crosslinking within the fluid that gives a gel its structure (hardness). In this way gels may be a dispersion of molecules of a liquid within a solid in which liquid particles are dispersed in the solid medium.

The term "hydrogen-bond crosslinking gelling agent" refers to a gelling agent that forms non-covalent crosslinking bonds or physical crosslinking bonds via hydrogen bonding. Hydrogen bonding is a type of electrostatic dipole-dipole attraction between molecules, not a covalent bond to a hydrogen atom. It results from the attractive force between a hydrogen atom covalently bonded to a very electronegative atom such as a N, O, or F atom and another very electronegative atom.

The term "ionic crosslinking gelling agent" refers to a gelling agent that forms non-covalent crosslinking bonds or physical crosslinking bonds via ionic bonding. Ionic crosslinking involves the association of polymer chains by non-covalent interactions. A crosslinked network is formed when multivalent molecules of opposite charges electrostatically attract each other giving rise to a crosslinked polymeric network.

The gel composition described herein may be combined with an aerosol-generating device to deliver an alkaloid compound, or a cannabinoid compound, or both an alkaloid compound and a cannabinoid compound to a consumer. The gel composition described herein may be combined with an aerosol-generating device to deliver nicotine to a consumer. The gel composition may be packaged separately (as a gel consumable) from or not form a portion of the aerosol-generating device. A depleted gel consumable may be replaced with a full charged gel consumable within the aerosol-generating device. A plurality of these gel consumables may be combined with an aerosol-generating device to form a kit.

The gel composition described herein may be packaged in a sealed or closed container for transit from manufacture to consumption by the consumer. The gel composition has an exposed surface that is in contact with a head space defined by the interior surface of the container. The head space may have a relative humidity that equilibrates with the gel composition. The head space relative humidity may be substantially similar to the (local) humidity provided by the gel composition.

The gel composition described herein may be packaged or contained within an aerosol-generating article. The term "aerosol-generating article" is used to describe an article able to generate, or release, an aerosol. The aerosol-generating article may define a tubular element that may be formed of fluid permeable materials, such as paper, cardboard, cotton, cellulose acetate, viscose, poly-lactic acid, or combinations thereof. The tubular element may include a wrapper. The wrapper may be formed of fluid permeable materials, such as paper, cardboard, cotton, or combinations thereof.

A "tubular element" describes a component suitable for use in an aerosol-generating article. Ideally the tubular element may be longer in longitudinal length than in width but not necessarily as it may be one part of a multi-component item that ideally will be longer in its longitudinal length than its width. Typically, the tubular element is cylindrical but not necessarily. For example, the tubular element may have an oval, polygonal like triangular or rectangular, or random cross section.

The aerosol-generating article may have an open end, the proximal end, and a distal end, which may be open or closed in different specific embodiments. The tubular element contains the gel composition and is preferably disposed in proximity to the distal end of the aerosol-generating article. Applying a negative pressure on the open, proximal end causes at least one of an alkaloid compound and a cannabinoid compound from the gel composition, to be released. The aerosol-generating article defines at least one aperture between the proximal end and the distal end. The at least one aperture defines at least one fluid inlet, such that upon application of a negative pressure on the open, proximal end of the aerosol-generating article, fluid, for example air, enters the aerosol-generating article through the aperture. Preferably fluid, for example ambient air, drawn into the aerosol-generating article through the aperture, flows along the outer longitudinal passageway of the fluid guide towards the gel composition, in the proximity of the distal end of the aerosol-generating article. The fluid then flows through the inner longitudinal passageway of the fluid guide from the distal end to the proximal end and out of the aerosol-generating article at the open, proximal end.

By spacing the aperture from the distal end of the aerosol-generating article, the aperture is separated from the tubular element comprising the gel composition, reducing the likelihood of leakage of the gel composition through the aperture. Furthermore, by providing a passageway, for example the outer longitudinal passageway, for airflow from the aperture to the tubular element comprising the gel composition, the fluid from the aperture may be directed towards the gel composition and the fluid guide may act as a further obstacle between the gel composition and the aperture. The advantage of this is to further reduce the likelihood of leakage of the gel composition through the aperture. In addition, the inner longitudinal passageway of the fluid guide provides a pathway for fluid, for example air, and material or vapour generated, or released from the tubular element, to be drawn out of the aerosol-generating article through the open, proximal end.

Preferably the aerosol-generating article is generally cylindrical. This easily enables a smooth flow of the aerosol. The aerosol-generating article may have an outer diameter, for example, between 4 millimetres and 15 millimetres, between 5 millimetres and 10 millimetres, or between 6 millimetres and 8 millimetres. The aerosol-generating article may have a length, for example, between 10 millimetres and 60 millimetres, between 15 millimetres and 50 millimetres, or between 20 millimetres and 45 millimetres.

The resistance to draw (RTD) of the aerosol-generating article will vary depending on, among other things, the length and dimensions of the passageways, the size of the apertures, the dimensions of the most constricted cross-sectional area of the internal passageway, and the materials used. In specific embodiments the RTD of the aerosol-generating article is between 50 millimetre of water (mm $H_2O$) and 140 millimetre of water (mm $H_2O$), between 60 millimetre of water (mm $H_2O$) and 120 millimetre of water (mm $H_2O$), or between 80 millimetre of water (mm $H_2O$) and 100 millimetre of water (mm $H_2O$). The RTD of the article refers to the static pressure difference between the one or more apertures and the mouth end of the article when it is traversed by an inner longitudinal passageway under steady conditions in which the volumetric flow is 17.5 millilitres per second at the mouth end. The RTD of a specimen can be measured using the method set out in ISO Standard 6565:2002.

In specific embodiments the aerosol-generating article comprises plastic material; a metal material; a cellulosic material, such as cellulose acetate; paper; cardboard; cotton; or combinations thereof.

In specific embodiments the fluid guide comprises plastic material, a metal material, a cellulosic material, such as cellulose acetate, paper, cardboard, or combinations thereof.

In combination with specific embodiments the wrapper comprises more than one material. In specific embodiments the wrapper, or a portion thereof, comprises, a metal material, a plastic material, cardboard, paper, cotton, or combinations thereof. When the wrapper comprises cardboard or paper, the apertures may be formed by laser cuts.

A wrapper provides strength and structural rigidity for the aerosol-generating article. When paper or cardboard is used for the wrapper and a high degree of stiffness is desired it preferably has a basis weight greater than 60 grams per square metre. One such wrapper may provide high structural rigidity. The wrapper may resist deformation on the outside of the aerosol-generating article at the location where, if present, the restrictor is embedded within the aerosol-generating article, or in other locations for example, in cavities (if present) where there is less structural support. In some embodiments, the tubular element wrapper comprises a metal layer. The metal layer may be used to concentrate an externally applied energy to heat the tubular member, for example, the metal layer may act as susceptor for an electromagnetic field or collect radiation energy supplied by an external heat source. If an internal heat source is present, the metal layer may prevent heat from leaving the tubular element through the wrapper, thus increasing the efficiency of the heating. It may also provide for a uniform distribution of heat along the periphery of the tubular member.

In specific embodiments the aerosol-generating article comprises a seal between an exterior of the fluid guide and an interior of a wrapper. The wrapper may then be securely attached to the fluid guide. It need not create a fluid impermeable seal.

In specific embodiments, the aerosol-generating article comprises a mouthpiece. The mouthpiece may comprise the fluid guide, or a portion thereof, and may form at least a proximal portion of the wrapper of the aerosol-generating article. The mouthpiece may connect with the wrapper, or a distal portion of the wrapper, in any suitable manner, such as through interference fit, threaded engagement, or the like. The mouthpiece can be the portion of the aerosol-generating article that can include a filter, or in some cases the mouthpiece can be defined by the extent of the tipping paper, if present. In other embodiments, the mouthpiece can be defined as a portion of the article extending 40 millimetres from the mouth end of the aerosol-generating article, or, extending 30 millimetres from the mouth end of the aerosol-generating article.

The tubular element, containing the gel composition, may be placed in the aerosol-generating article in proximity to the distal end prior to final assembly of the aerosol-generating article.

Once fully assembled, the aerosol-generating article defines a fluid path through which fluid can flow. When a negative pressure is provided at the mouth end (proximal end) of the aerosol-generating article, fluid enters the aerosol-generating article through an aperture in the wrapper (or fluid guide, or both), then flows through the outer longitudinal passageway towards the distal end of the aerosol-generating article. There it may entrain aerosol, optionally generated by heating of the tubular element holding the gel composition. The fluid with entrained aerosol may then flow through the inner longitudinal passageway of the fluid guide and through the open mouth end of the aerosol-generating article.

Preferably the aerosol-generating article is configured to be received by an aerosol-generating device such that a heating element of the aerosol-generating device may heat the section of the aerosol-generating article that comprises the tubular element. For example, the tubular element may be the distal end of the aerosol-generating article should the tubular element, containing the gel composition, be disposed at or near to the distal end of the aerosol-generating article.

Preferably the aerosol-generating article may be shaped and sized for use with a suitably, correspondingly shaped and sized aerosol-generating device comprising a receptacle for receiving the aerosol-generating article and a heating element configured and positioned to heat the section of the aerosol-generating article that comprises the tubular element containing the gel composition.

The aerosol-generating device preferably comprises control electronics operably coupled to the heating element. The control electronics may be configured to control heating of the heating element. The control electronics may be internal to a housing of the device.

A gel composition, according to the disclosure, includes: an alkaloid compound, or a cannabinoid compound, or both an alkaloid compound and a cannabinoid compound; an aerosol former; a viscosifying agent; a hydrogen-bond crosslinking gelling agent; an ionic crosslinking gelling agent; and an acid. The gel composition may further include divalent cations.

A gel composition, according to the disclosure, includes: nicotine; an aerosol former; a viscosifying agent; a hydrogen-bond crosslinking gelling agent; an ionic crosslinking gelling agent; and an acid. The gel composition may further include divalent cations.

The gel composition includes an aerosol-former. Ideally the aerosol-former is substantially resistant to thermal degradation at the operating temperature of the associated aerosol-generating device. Suitable aerosol-formers include, but are not limited to: polyhydric alcohols, such as triethylene glycol, 1, 3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Polyhydric alcohols or mixtures thereof, may be one or more of triethylene glycol, 1, 3-butanediol and, glycerine (glycerol or propane-1,2,3-triol) or polyethylene glycol. The aerosol-former is preferably glycerol.

The gel composition may include a majority of an aerosol-former. The gel composition may include a mixture of water and the aerosol-former where the aerosol-former forms a majority (by weight) of the gel composition. The aerosol-former may form at least about 50% wt. of the gel composition. The aerosol-former may form at least about 60% wt., or at least about 65% wt., or at least about 70% wt. of the gel composition. The aerosol-former may form about 70% wt. to about 80% wt. of the gel composition. The aerosol-former may form about 70% wt. to about 75% wt. of the gel composition.

The gel composition may include a majority of glycerol. The gel composition may include a mixture of water and the glycerol where the glycerol forms a majority (by weight) of the gel composition. The glycerol may form at least about 50% wt. of the gel composition. The glycerol may form at least about 60% wt., or at least about 65% wt., or at least about 70% wt. of the gel composition. The glycerol may form about 70% wt. to about 80% wt. of the gel composition. The glycerol may form about 70% wt. to about 75% wt. of the gel composition.

The gel composition preferably comprises no water or a low level of water. When the gel composition comprises no water or a low level of water, the gel composition may comprise a higher level of other compounds such as aerosol-former, gelling agent, viscosifying agent, and nicotine. Also, gel composition comprising no water or a low level of water are easier and require less energy to vaporize. Aerosols formed from a gel composition comprising no water or a low level of water can be perceived as less hot by the user. Preferably the gel composition comprises less than about 40% wt., preferably less than about 30% wt., preferably less than about 25% wt. water. The gel composition may comprise less than about 20% wt. or less than about 15% wt. or less than about 10% wt. or less than about 5% wt. of water.

The gel composition preferably comprises some water. The gel composition is more stable when the composition comprises some water. Preferably the gel composition comprises at least about 1% wt., or at least about 2% wt., or at least about 5% wt. of water. Preferably the gel composition comprises at least about 10% wt. or at least about 15% wt. water.

Preferably the gel composition comprises between about 8% wt. to about 32% wt. water. Preferably the gel composition comprises from about 14% wt. to about 26 wt. % water. Preferably the gel composition comprises from about 18% wt. to about 22% wt. water. Preferably the gel composition comprises about 20% wt. water. Preferably the gel composition comprises from about 15% wt. to about 25% wt. water.

The gel composition may include a specific ratio of water to glycerol content to maintain an equilibrated local humidity with ambient environmental humidity. This range of water to glycerol content may provide the properties needed to maintain a gel composition. The gel composition will not substantially flow and substantially maintains its shape over time. The gel composition will not substantially flow and substantially maintains its mass over time. The gel will not substantially release water (sweat) or absorb water over time when exposed to ambient environmental or storage conditions.

Preferably the gel composition comprises an aerosol former or glycerol to water ratio in a range from about 10:1 to about 2:1, or in a range from about 5:1 to about 3:1. Preferably the gel composition comprises an aerosol former or glycerol to water ratio in a range from about 4.5:1 to about 3.5:1.

The gel composition may include gelling agents being the hydrogen-bond crosslinking gelling agent and the ionic crosslinking gelling agent. The gel composition may further include a viscosifying agent. The gelling agents may form a solid medium in which the aerosol-former may be dispersed. The gelling agents may form a solid medium in which the aerosol-former and water may be dispersed. The viscosifying agent combined with the hydrogen-bond crosslinking gelling agent and the ionic crosslinking gelling agent appears to surprisingly support the solid medium and maintain the gel composition even when the gel composition comprises a high level of glycerol.

The gel composition may include the gelling agents in a range from about 0.4% to about 10% by weight. Preferably the composition includes the gelling agents in a range from about 0.5% to about 8% by weight. Preferably the composition includes the gelling agents in a range from about 1% to about 6% by weight. Preferably the composition includes the gelling agents in a range from about 2% to about 4% by weight. Preferably the composition includes the gelling agents in a range from about 2% to about 3% by weight.

The gel composition includes the viscosifying agent in a range from about 0.2% to about 5% by weight. Preferably the composition includes the viscosifying agent in a range from about 0.5% to about 3% by weight. Preferably the composition includes the viscosifying agent in a range from about 0.5% to about 2% by weight. Preferably the composition includes the viscosifying agent in a range from about 1% to about 2% by weight.

The gel composition may include the viscosifying agent, hydrogen-bond crosslinking gelling agent, and ionic crosslinking gelling agent being present in the gel composition in a total amount from about 1% wt. to about 8% wt. Preferably the gel composition may include the viscosifying agent, hydrogen-bond crosslinking gelling agent, and ionic crosslinking gelling agent being present in the gel composition in a total amount from about 2% wt. to about 6% wt. Preferably the gel composition may include the viscosifying agent, hydrogen-bond crosslinking gelling agent, and ionic crosslinking gelling agent being present in the gel composition in a total amount from about 3% wt. to about 5% wt.

The gel composition may include the viscosifying agent, hydrogen-bond crosslinking gelling agent, and ionic crosslinking gelling agent each independently present in the gel composition in a range from about 0.3% wt. to about 3% wt. Preferably the gel composition may include the viscosifying agent, hydrogen-bond crosslinking gelling agent, and ionic crosslinking gelling agent each independently present in the gel composition in a range from about 0.5% wt. to about 2% wt. Preferably the gel composition may include the viscosifying agent, hydrogen-bond crosslinking gelling agent, and ionic crosslinking gelling agent each independently present in the gel composition in a range from about 1% wt. to about 2% wt.

The viscosifying agent may include one or more of xanthan gum, carboxymethyl-cellulose, microcrystalline cellulose, methyl cellulose, gum Arabic, guar gum, lambda carrageenan, or starch. The viscosifying agent may preferably include xanthan gum.

The gel composition may include xanthan gum in a range from about 0.2% to about 5% by weight. Preferably the xanthan gum may be in a range from about 0.5% to about 3% by weight. Preferably the xanthan gum may be in a range from about 0.5% to about 2% by weight. Preferably the xanthan gum may be in a range from about 1% to about 2% by weight.

The gel composition may include carboxymethyl-cellulose in a range from about 0.2% to about 5% by weight. Preferably the carboxymethyl-cellulose may be in a range from about 0.5% to about 3% by weight. Preferably the carboxymethyl-cellulose may be in a range from about 0.5% to about 2% by weight. Preferably the carboxymethyl-cellulose may be in a range from about 1% to about 2% by weight.

The gel composition may include microcrystalline cellulose in a range from about 0.2% to about 5% by weight. Preferably the microcrystalline cellulose may be in a range from about 0.5% to about 3% by weight. Preferably the microcrystalline cellulose may be in a range from about 0.5% to about 2% by weight. Preferably the microcrystalline cellulose may be in a range from about 1% to about 2% by weight.

The gel composition may include methyl cellulose in a range from about 0.2% to about 5% by weight. Preferably the methyl cellulose may be in a range from about 0.5% to about 3% by weight. Preferably the methyl cellulose may be in a range from about 0.5% to about 2% by weight. Preferably the methyl cellulose may be in a range from about 1% to about 2% by weight.

The gel composition may include gum Arabic in a range from about 0.2% to about 5% by weight. Preferably the gum Arabic may be in a range from about 0.5% to about 3% by weight. Preferably the gum Arabic may be in a range from about 0.5% to about 2% by weight. Preferably the gum Arabic may be in a range from about 1% to about 2% by weight.

The gel composition may include guar gum in a range from about 0.2% to about 5% by weight. Preferably the guar gum may be in a range from about 0.5% to about 3% by weight. Preferably the guar gum may be in a range from about 0.5% to about 2% by weight. Preferably the guar gum may be in a range from about 1% to about 2% by weight.

The gel composition may include lambda carrageenan in a range from about 0.2% to about 5% by weight. Preferably the lambda carrageenan may be in a range from about 0.5% to about 3% by weight. Preferably the lambda carrageenan may be in a range from about 0.5% to about 2% by weight. Preferably the lambda carrageenan may be in a range from about 1% to about 2% by weight.

The gel composition may include starch in a range from about 0.2% to about 5% by weight. Preferably the starch may be in a range from about 0.5% to about 3% by weight. Preferably the starch may be in a range from about 0.5% to about 2% by weight. Preferably the starch may be in a range from about 1% to about 2% by weight.

The hydrogen-bond crosslinking gelling agent may include one or more of a galactomannan, gelatin, agarose, or konjac gum, or agar. The hydrogen-bond crosslinking gelling agent may preferably include agar.

The gel composition includes the hydrogen-bond crosslinking gelling agent in a range from about 0.3% to about 5% by weight. Preferably the composition includes the hydrogen-bond crosslinking gelling agent in a range from about 0.5% to about 3% by weight. Preferably the composition includes the hydrogen-bond crosslinking gelling agent in a range from about 1% to about 2% by weight.

The gel composition may include a galactomannan in a range from about 0.2% to about 5% by weight. Preferably the galactomannan may be in a range from about 0.5% to about 3% by weight. Preferably the galactomannan may be in a range from about 0.5% to about 2% by weight. Preferably the galactomannan may be in a range from about 1% to about 2% by weight.

The gel composition may include a gelatin in a range from about 0.2% to about 5% by weight. Preferably the gelatin may be in a range from about 0.5% to about 3% by weight. Preferably the gelatin may be in a range from about 0.5% to about 2% by weight. Preferably the gelatin may be in a range from about 1% to about 2% by weight.

The gel composition may include agarose in a range from about 0.2% to about 5% by weight. Preferably the agarose may be in a range from about 0.5% to about 3% by weight. Preferably the agarose may be in a range from about 0.5% to about 2% by weight. Preferably the agarose may be in a range from about 1% to about 2% by weight.

The gel composition may include konjac gum in a range from about 0.2% to about 5% by weight. Preferably the konjac gum may be in a range from about 0.5% to about 3% by weight. Preferably the konjac gum may be in a range from about 0.5% to about 2% by weight. Preferably the konjac gum may be in a range from about 1% to about 2% by weight.

The gel composition may include agar in a range from about 0.2% to about 5% by weight. Preferably the agar may be in a range from about 0.5% to about 3% by weight. Preferably the agar may be in a range from about 0.5% to about 2% by weight. Preferably the agar may be in a range from about 1% to about 2% by weight.

The ionic crosslinking gelling agent may include low acyl gellan, pectin, kappa carrageenan, iota carrageenan or alginate. The ionic crosslinking gelling agent may preferably include low acyl gellan.

The gel composition may include the ionic crosslinking gelling agent in a range from about 0.3% to about 5% by weight. Preferably the composition includes the ionic crosslinking gelling agent in a range from about 0.5% to about 3% by weight. Preferably the composition includes the ionic crosslinking gelling agent in a range from about 1% to about 2% by weight.

The gel composition may include low acyl gellan in a range from about 0.2% to about 5% by weight. Preferably the low acyl gellan may be in a range from about 0.5% to about 3% by weight. Preferably the low acyl gellan may be in a range from about 0.5% to about 2% by weight. Preferably the low acyl gellan may be in a range from about 1% to about 2% by weight.

The gel composition may include pectin in a range from about 0.2% to about 5% by weight. Preferably the pectin may be in a range from about 0.5% to about 3% by weight. Preferably the pectin may be in a range from about 0.5% to about 2% by weight. Preferably the pectin may be in a range from about 1% to about 2% by weight.

The gel composition may include kappa carrageenan in a range from about 0.2% to about 5% by weight. Preferably the kappa carrageenan may be in a range from about 0.5% to about 3% by weight. Preferably the kappa carrageenan may be in a range from about 0.5% to about 2% by weight. Preferably the kappa carrageenan may be in a range from about 1% to about 2% by weight.

The gel composition may include iota carrageenan in a range from about 0.2% to about 5% by weight. Preferably the iota carrageenan may be in a range from about 0.5% to about 3% by weight. Preferably the iota carrageenan may be in a range from about 0.5% to about 2% by weight. Preferably the iota carrageenan may be in a range from about 1% to about 2% by weight.

The gel composition may include alginate in a range from about 0.2% to about 5% by weight. Preferably the alginate may be in a range from about 0.5% to about 3% by weight. Preferably the alginate may be in a range from about 0.5% to about 2% by weight. Preferably the alginate may be in a range from about 1% to about 2% by weight.

The gel composition may include the hydrogen-bond crosslinking gelling agent and ionic crosslinking gelling agent in a ratio of about 3:1 to about 1:3. Preferably the gel composition may include the hydrogen-bond crosslinking gelling agent and ionic crosslinking gelling agent in a ratio of about 2:1 to about 1:2. Preferably the gel composition may include the hydrogen-bond crosslinking gelling agent and ionic crosslinking gelling agent in a ratio of about 1:1.

The gel composition may include the hydrogen-bond crosslinking gelling agent and the viscosifying agent in a ratio of about 3:1 to about 1:3. Preferably the gel composition may include the hydrogen-bond crosslinking gelling agent and viscosifying agent in a ratio of about 2:1 to about 1:2. Preferably the gel composition may include the hydrogen-bond crosslinking gelling agent and viscosifying agent in a ratio of about 1:1.

The gel composition may include the ionic crosslinking gelling agent and the viscosifying agent in a ratio of about 3:1 to about 1:3. Preferably the gel composition may include the ionic crosslinking gelling agent and viscosifying agent in a ratio of about 2:1 to about 1:2. Preferably the gel composition may include the ionic crosslinking gelling agent and viscosifying agent in a ratio of about 1:1.

The gel composition may include the gelling agents and an alkaloid compound in a ratio of about 3:1 to about 1:3. Preferably the gel composition may include the gelling agents and an alkaloid compound in a ratio of about 2:1 to about 1:2. Preferably the gel composition may include the gelling agents and an alkaloid compound in a ratio of about 1:1.

The gel composition may include the viscosifying agent and an alkaloid compound in a ratio of about 1:1 to about 1:5. Preferably the gel composition may include the viscosifying agent and an alkaloid compound in a ratio of about 1:1 to about 1:3. Preferably the gel composition may include the viscosifying agent and an alkaloid compound in a ratio of about 1:2.

The gel composition may include an alkaloid compound and water in a ratio of about 1:5 to about 1:20. Preferably the gel composition may include an alkaloid compound and water in a ratio of about 1:8 to about 1:12. Preferably the gel composition may include an alkaloid compound and water in a ratio of about 1:10.

The gel composition may include an alkaloid compound and glycerol in a ratio of about 1:50 to about 1:25. Preferably the gel composition may include an alkaloid compound and glycerol in a ratio of about 1:40 to about 1:30. Preferably the gel composition may include an alkaloid compound and glycerol in a ratio of about 1:36.

The gel composition may include the gelling agents and nicotine in a ratio of about 3:1 to about 1:3. Preferably the gel composition may include the gelling agents and nicotine in a ratio of about 2:1 to about 1:2. Preferably the gel composition may include the gelling agents and nicotine in a ratio of about 1:1.

The gel composition may include the viscosifying agent and nicotine in a ratio of about 1:1 to about 1:5. Preferably the gel composition may include the viscosifying agent and nicotine in a ratio of about 1:1 to about 1:3. Preferably the gel composition may include the viscosifying agent and nicotine in a ratio of about 1:2.

The gel composition may include nicotine and water in a ratio of about 1:5 to about 1:20. Preferably the gel composition may include the nicotine and water in a ratio of about 1:8 to about 1:12. Preferably the gel composition may include the nicotine and water in a ratio of about 1:10.

The gel composition may include nicotine and glycerol in a ratio of about 1:50 to about 1:25. Preferably the gel composition may include the nicotine and glycerol in a ratio of about 1:40 to about 1:30. Preferably the gel composition may include the nicotine and glycerol in a ratio of about 1:36.

The gel composition may include gelling agents and glycerol in a ratio of about 1:50 to about 1:25. Preferably the gel composition may include the gelling agents and glycerol in a ratio of about 1:40 to about 1:30. Preferably the gel composition may include the gelling agents and glycerol in a ratio of about 1:36.

The gel composition may include viscosifying agent and glycerol in a ratio of about 1:90 to about 1:40. Preferably the gel composition may include the viscosifying agent and glycerol in a ratio of about 1:80 to about 1:65. Preferably the gel composition may include the gelling agents and glycerol in a ratio of about 1:73.

The gel composition may include the gelling agents and a cannabinoid compound in a ratio of about 3:1 to about 1:3. Preferably the gel composition may include the gelling agents and a cannabinoid compound in a ratio of about 2:1 to about 1:2. Preferably the gel composition may include the gelling agents and a cannabinoid compound in a ratio of about 1:1.

The gel composition may include the viscosifying agent and a cannabinoid compound in a ratio of about 1:1 to about 1:5. Preferably the gel composition may include the viscosifying agent and a cannabinoid compound in a ratio of about 1:1 to about 1:3. Preferably the gel composition may include the viscosifying agent and a cannabinoid compound in a ratio of about 1:2.

The gel composition may include a cannabinoid compound and water in a ratio of about 1:5 to about 1:20. Preferably the gel composition may include a cannabinoid compound and water in a ratio of about 1:8 to about 1:12. Preferably the gel composition may include a cannabinoid compound and water in a ratio of about 1:10.

The gel composition may include a cannabinoid compound and glycerol in a ratio of about 1:50 to about 1:25. Preferably the gel composition may include a cannabinoid compound and glycerol in a ratio of about 1:40 to about 1:30. Preferably the gel composition may include a cannabinoid compound and glycerol in a ratio of about 1:36.

The gel composition may include the gelling agents and both an alkaloid compound and a cannabinoid compound in a ratio of about 3:1 to about 1:3. Preferably the gel composition may include the gelling agents and both an alkaloid compound and a cannabinoid compound in a ratio of about 2:1 to about 1:2. Preferably the gel composition may include the gelling agents and both an alkaloid compound and a cannabinoid compound in a ratio of about 1:1.

The gel composition may include the viscosifying agent and both an alkaloid compound and a cannabinoid compound in a ratio of about 1:1 to about 1:5. Preferably the gel composition may include the viscosifying agent and both an alkaloid compound and a cannabinoid compound in a ratio of about 1:1 to about 1:3. Preferably the gel composition may include the viscosifying agent and both an alkaloid compound and a cannabinoid compound in a ratio of about 1:2.

The gel composition may include both an alkaloid compound and a cannabinoid compound and water in a ratio of about 1:5 to about 1:20. Preferably the gel composition may include both an alkaloid compound and a cannabinoid compound and water in a ratio of about 1:8 to about 1:12. Preferably the gel composition may include both an alkaloid compound and a cannabinoid compound and water in a ratio of about 1:10.

The gel composition may include both an alkaloid compound and a cannabinoid compound and glycerol in a ratio of about 1:50 to about 1:25. Preferably the gel composition may include both an alkaloid compound and a cannabinoid compound and glycerol in a ratio of about 1:40 to about 1:30. Preferably the gel composition may include both an alkaloid compound and a cannabinoid compound and glycerol in a ratio of about 1:36.

The gel composition may further include a divalent cation. Preferably the divalent cation includes calcium ions, such as calcium lactate in solution. Divalent cations (such as calcium ions) may assist in the gel formation of compositions that include gelling agents such as the ionic crosslinking gelling agent, for example. The ion effect may assist in the gel formation. The divalent cation may be present in the gel composition in a range from about 0.1 to about 1% by weight, or about 0.5% wt.

The gel composition may further include an acid. The acid may comprise a carboxylic acid. The carboxylic acid may include a ketone group. Preferably the carboxylic acid may include a ketone group having less than about 10 carbon atoms, or less than about 6 carbon atoms or less than about 4 carbon atoms, such as levulinic acid or lactic acid. Preferably this carboxylic acid has three carbon atoms (such as lactic acid). Lactic acid surprisingly improves the stability of the gel composition even over similar carboxylic acids. The carboxylic acid may assist in the gel formation. The carboxylic acid may reduce variation of the alkaloid compound concentration, or the cannabinoid compound concentration, or both the alkaloid compound concentration and the cannabinoid compound within the gel composition during storage. The carboxylic acid may reduce variation of the nicotine concentration within the gel composition during storage.

The gel composition may include a carboxylic acid in a range from about 0.1% to about 5% by weight. Preferably the carboxylic acid may be in a range from about 0.5% to about 3% by weight. Preferably the carboxylic acid may be in a range from about 0.5% to about 2% by weight. Preferably the carboxylic acid may be in a range from about 1% to about 2% by weight.

The gel composition may include lactic acid in a range from about 0.1% to about 5% by weight. Preferably the lactic acid may be in a range from about 0.5% to about 3% by weight. Preferably the lactic acid may be in a range from about 0.5% to about 2% by weight. Preferably the lactic acid may be in a range from about 1% to about 2% by weight.

The gel composition may include levulinic acid in a range from about 0.1% to about 5% by weight. Preferably the levulinic acid may be in a range from about 0.5% to about 3% by weight. Preferably the levulinic acid may be in a range from about 0.5% to about 2% by weight. Preferably the levulinic acid may be in a range from about 1% to about 2% by weight.

The gel composition may include the carboxylic acid and an alkaloid compound in a ratio of about 2:1 to about 1:2. Preferably the gel composition may include the carboxylic acid and an alkaloid compound in a ratio of about 1:1.5 to about 1.5:1. Preferably the gel composition may include the carboxylic acid and an alkaloid compound in a ratio of about 1:1.

The gel composition may include the carboxylic acid and nicotine in a ratio of about 2:1 to about 1:2. Preferably the gel composition may include the carboxylic acid and nicotine in a ratio of about 1:1.5 to about 1.5:1. Preferably the gel composition may include the carboxylic acid and nicotine in a ratio of about 1:1.

The gel composition may include the carboxylic acid and a cannabinoid compound in a ratio of about 2:1 to about 1:2. Preferably the gel composition may include the carboxylic acid and a cannabinoid compound in a ratio of about 1:1.5 to about 1.5:1. Preferably the gel composition may include the carboxylic acid and a cannabinoid compound in a ratio of about 1:1.

The gel composition may include the carboxylic acid and both an alkaloid compound and a cannabinoid compound in a ratio of about 2:1 to about 1:2. Preferably the gel composition may include the carboxylic acid and both an alkaloid compound and a cannabinoid compound in a ratio of about 1:1.5 to about 1.5:1. Preferably the gel composition may include the carboxylic acid and both an alkaloid compound and a cannabinoid compound in a ratio of about 1:1.

The gel composition may include the carboxylic acid and viscosifying agent in a ratio of about 2:1 to about 1:2. Preferably the gel composition may include the carboxylic acid and viscosifying agent in a ratio of about 1:1.5 to about 1.5:1. Preferably the gel composition may include the carboxylic acid and viscosifying agent in a ratio of about 1:1.

The gel composition may include the carboxylic acid and gelling agents in a ratio of about 2:1 to about 1:4. Preferably the gel composition may include the carboxylic acid and gelling agents in a ratio of about 1:1 to about 1:3. Preferably the gel composition may include the carboxylic acid and gelling agents in a ratio of about 1:2.

The gel composition may include carboxylic acid and glycerol in a ratio of about 1:70 to about 1:30. Preferably the gel composition may include the carboxylic acid and glycerol in a ratio of about 1:60 to about 1:50. Preferably the gel composition may include carboxylic acid and glycerol in a ratio of about 1:55.

The gel composition may include carboxylic acid and water in a ratio of about 1:30 to about 1:5. Preferably the gel composition may include the carboxylic acid and water in a ratio of about 1:20 to about 1:10. Preferably the gel composition may include carboxylic acid and water in a ratio of about 1:15.

An alkaloid compound, or a cannabinoid compound, or both an alkaloid compound and a cannabinoid compound is included in the gel compositions. The gel composition includes about 0.5% to about 10% wt. of an alkaloid compound, or about 0.5% to about 10% wt. of a cannabinoid compound, or both an alkaloid compound and a cannabinoid compound in a total amount from about 0.5% to about 10% wt. The gel composition may include about 0.5% to about 5% wt. of an alkaloid compound, or about 0.5% to about 5% wt. of a cannabinoid compound, or both an alkaloid compound and a cannabinoid compound in a total amount from about 0.5% to about 5% wt. Preferably the gel composition includes about 1% to about 3% wt. of an alkaloid compound, or about 1% to about 3% wt. of a cannabinoid compound, or both an alkaloid compound and a cannabinoid compound in a total amount from about 1% to about 3% wt. The gel composition may preferably include about 1.5% to about 2.5% wt. of an alkaloid compound, or about 1.5% to about 2.5% wt. of a cannabinoid compound, or both an alkaloid compound and a cannabinoid compound in a total amount from about 1.5% to about 2.5% wt. The gel composition may preferably include about 2% wt. of an alkaloid compound, or about 2% wt. of a cannabinoid compound, or both an alkaloid compound and a cannabinoid compound in a total amount of about 2% wt. The alkaloid compound component of the gel formulation may be the most volatile component of the gel formulation. In some aspects water may be the most volatile component of the gel formulation and the alkaloid compound component of the gel formulation may be the second most volatile component of the gel formulation. The cannabinoid compound component of the gel formulation may be the most volatile component of the gel formulation. In some aspects water may be the most volatile component of the gel formulation and the alkaloid compound component of the gel formulation may be the second most volatile component of the gel formulation.

Preferably nicotine is included in the gel compositions. The nicotine may be added to the composition in a free base form or a salt form. The gel composition includes about 0.5% to about 10% wt., nicotine, or about 0.5% to about 5% wt. nicotine. Preferably the gel composition includes about 1% to about 3% wt., nicotine, or about 1.5% to about 2.5% wt. nicotine, or about 2% wt. nicotine. The nicotine component of the gel formulation may be the most volatile component of the gel formulation. In some aspects water may be the most volatile component of the gel formulation and the nicotine component of the gel formulation may be the second most volatile component of the gel formulation.

In embodiments where agar is used as the hydrogen-bond crosslinking gelling agent, the gel composition comprises between 0.2 and 5 percent by weight, preferably between 0.5 and 2 percent by weight, agar. Preferably this gel composition may include between 0.2 and 5 percent by weight, preferably between 0.5 and 2 percent by weight, ionic crosslinking gelling agent, such as low acyl gellan or alginate. Preferably this gel composition may include between 0.2 and 5 percent by weight, preferably between 0.5 and 2 percent by weight, viscosifying agent, such as xanthan gum. Preferably the gel further comprises between 0.1 and 2 percent by weight of an alkaloid compound, or between 0.1 and 2 percent by weight of a cannabinoid compound, Preferably the gel further comprises between 0.1 and 2 percent by weight of an alkaloid compound, or between 0.1 and 2 percent by weight of a cannabinoid compound, or both an alkaloid compound and a cannabinoid compound in a total amount from 0.1 to 2 percent by weight. Preferably the gel further comprises between 0.1 and 2 percent by weight nicotine. Preferably the gel further comprises between 70 percent and 80 percent by weight (or between 70 and 75 percent by weight) glycerol. Preferably the gel composition further comprises divalent cations such as calcium. In specific embodiments a remainder of the gel comprises water and optional flavorings. Preferably the gel composition further comprises an acid, or carboxylic acid such as lactic acid in an amount from about 0.5% to about 2.5% wt.

In embodiments where low acyl gellan is used as the ionic crosslinking gelling agent, the gel composition comprises between 0.2 and 5 percent by weight, preferably between 0.5 and 2 percent by weight, low acyl gellan. Preferably this gel composition may include between 0.2 and 5 percent by weight, preferably between 0.5 and 2 percent by weight, hydrogen-bond crosslinking gelling agent, such as agar. Preferably this gel composition may include between 0.2 and 5 percent by weight, preferably between 0.5 and 2 percent by weight, viscosifying agent, such as xanthan gum. Preferably the gel further comprises between 0.1 and 2 percent by weight of an alkaloid compound, or between 0.1 and 2 percent by weight of a cannabinoid compound, or both an alkaloid compound and a cannabinoid compound in a total amount from 0.1 to 2 percent by weight. Preferably the gel further comprises between 0.1 and 2 percent by weight nicotine. Preferably the gel further comprises between 70 percent and 80 percent by weight (or between 70 and 75 percent by weight) glycerol. Preferably the gel composition further comprises divalent cations such as calcium. In specific embodiments a remainder of the gel comprises water and optional flavorings. Preferably the gel composition further comprises an acid, or carboxylic acid such as lactic acid in an amount from about 0.5% to about 2.5% wt.

The gel composition may include: about 1.5% to about 2.5% wt. of an alkaloid compound, or about 1.5% to 2.5% wt. of a cannabinoid compound, or both an alkaloid compound and a cannabinoid compound in a total amount from about 1.5% to 2.5% wt.; about 70% to about 75% wt. glycerol; about 18 to about 22% wt. water; about 0.5% to about 2% wt. each of agar, xanthan gum and low acyl gellan; and calcium ions. Each of the xanthan gum, agar, and low acyl gellan may be present in the gel composition in substantially equal amounts by weight.

The gel composition may include: about 1.5% to about 2.5% wt. nicotine; about 70% to about 75% wt. glycerol; about 18 to about 22% wt. water; about 0.5% to about 2% wt. each of agar, xanthan gum and low acyl gellan; and calcium ions. Each of the xanthan gum, agar, and low acyl gellan may be present in the gel composition in substantially equal amounts by weight.

The gel composition may be heated (via an aerosol-generating device) to vaporize an alkaloid compound, or a cannabinoid compound, or both an alkaloid compound and a cannabinoid compound. The gel composition may be heated (via an aerosol-generating device) to vaporize nicotine. Heating the gel composition may not release a liquid phase.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

Reference will now be made to the drawings, which depict one or more aspects described in this disclosure. However, it will be understood that other aspects not depicted in the drawings fall within the scope and of this disclosure. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. The figures are presented for purposes of illustration and not limitation. Schematic drawings presented in the figures are not necessarily to scale.

Figure 1:
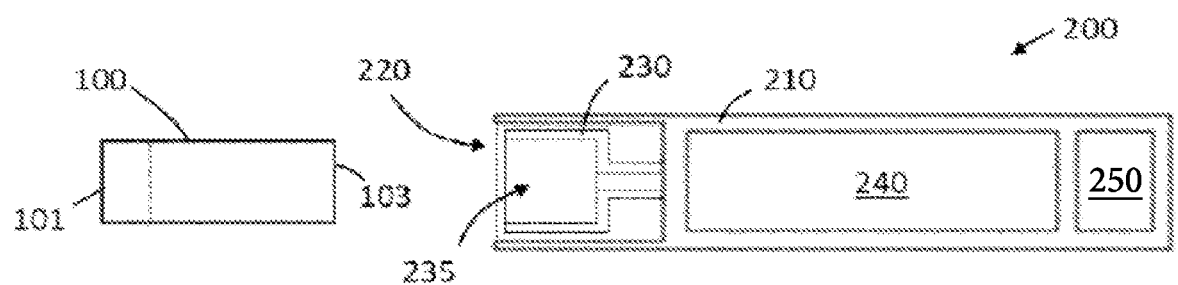
FIG. 1 is a schematic sectional view of an aerosol-generating device and a schematic side view of an aerosol-generating article that may be inserted into the aerosol-generating device.
Figure 2:
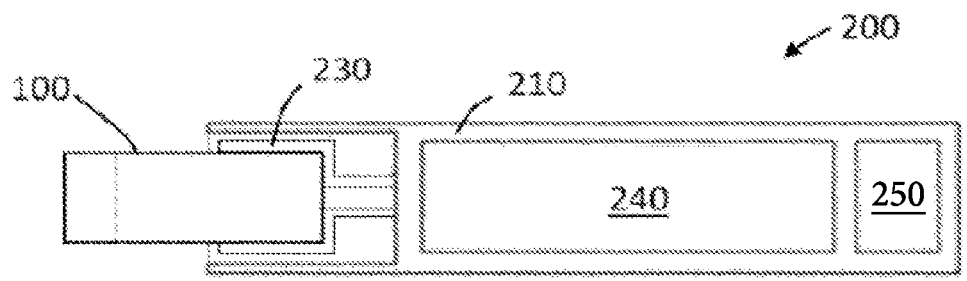
FIG. 2 is a schematic sectional view of the aerosol-generating device depicted in FIG. 1 and a schematic side view of the article depicted in FIG. 1 inserted into the aerosol-generating device.

FIGS. 1-2 illustrate an example of an aerosol-generating article 100 and aerosol-generating device 200. The aerosol-generating article 100 has a proximal or mouth end 101 and a distal end 103. In FIG. 2, the distal end 103 of the aerosol-generating article 100 is received in a receptacle 220 of the aerosol-generating device 200. The aerosol-generating device 200 includes a housing 210 defining the receptacle 220, which is configured to receive the aerosol-generating article 100. The aerosol-generating device 200 also includes a heating element 230 that forms a cavity 235 configured to receive the aerosol-generating article 100, preferably by interference fit. The heating element 230 may comprise an electrically resistive heating component. In addition, the device 200 includes a power supply 240 and control electronics 250 that cooperate to control heating of heating element 230.

The heating element 230 may heat the distal end 103 of the aerosol-generating article 100, which contains a tubular element 600 (not shown). In this example the tubular element 600 comprises the gel composition 500 comprising nicotine. Heating of the aerosol-generating article 100 causes the tubular element 600 comprising a gel composition 500 to generate an aerosol containing the nicotine, which can transfer out of the aerosol-generating article 100 at the proximal end 101.

FIGS. 1-2 do not show the exact heating mechanism.

In some examples the heating mechanism could be by conduction heating where the heat is transferred from the heating element 230 of the aerosol-generating device 200 to the aerosol-generating article 100. This can take place easily when the aerosol-generating article 100 is positioned in the receptacle 220 of the aerosol-generating device 200 and the distal end 103 (which is preferably the end where the tubular element 600 comprising gel composition 500 is located) and thus the aerosol-generating article 100 is in contact with the heating element 230 of the aerosol-generating device 200. In specific examples the heating element comprises a heating blade that protrudes from the aerosol-generating device 200 and is suitable for penetrating into the aerosol-generating article 100 to make direct contact with the gel composition 500 of the tubular element 600.

In this example the heating mechanism is by induction where the heating element emits radio-magnetic radiation which is absorbed by the tubular element when the aerosol-generating article 100 is position in the receptacle 220 of the aerosol-generating device 200.

Figure 3:
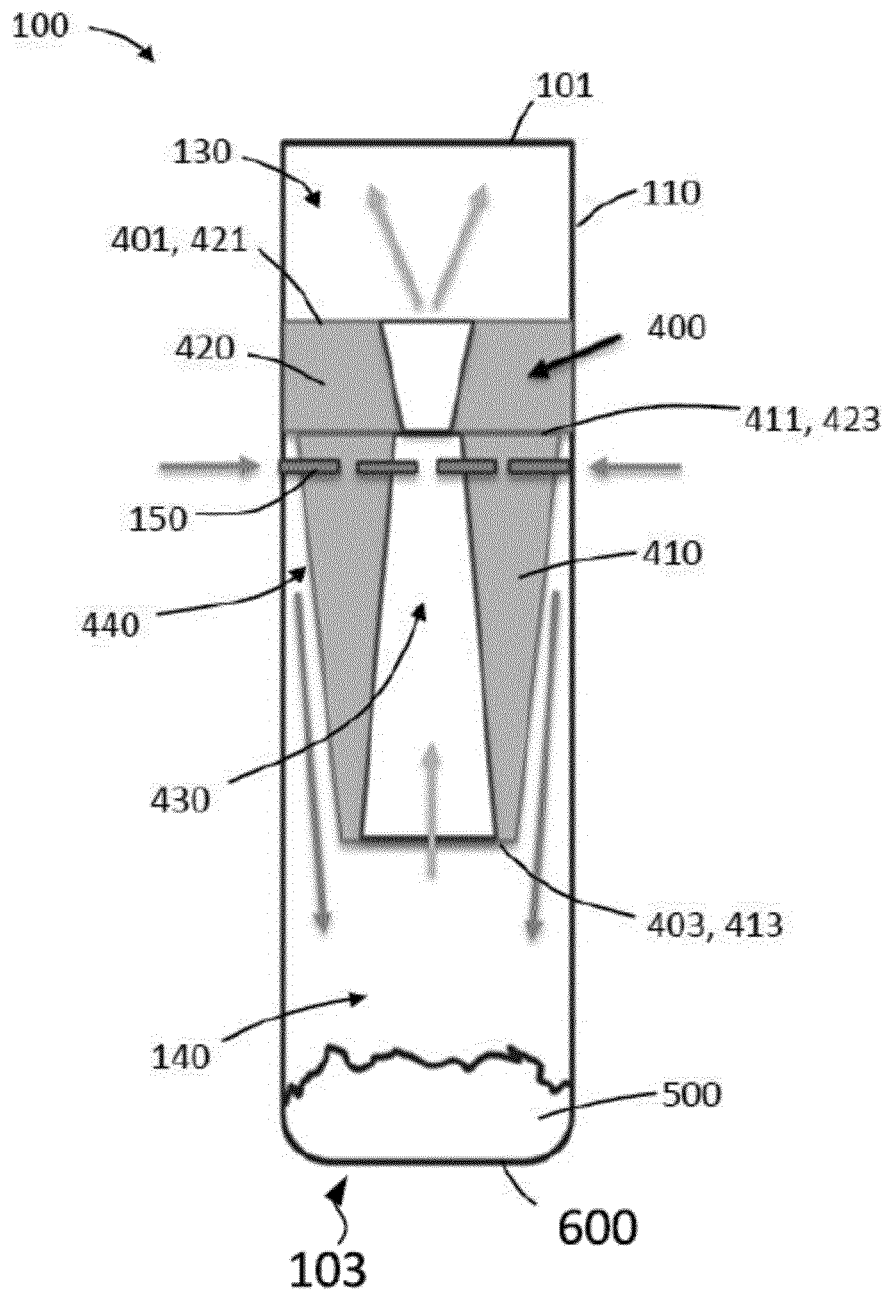
FIG. 3 is a schematic sectional view of an embodiment of an aerosol-generating article.

FIG. 3 depicts an embodiment of an aerosol-generating article 100 including a wrapper 110 and a fluid guide 400.

The fluid guide 400 has a proximal end 401, a distal end 403 and an inner longitudinal passageway 430 from the distal end 403 to the proximal end 401. The inner longitudinal passageway 430 has a first portion 410 and a second portion 420. The first portion 410 defines a first portion of the passageway 430, which extends from the distal end 413 of the first portion 410 to the proximal end 411 of the first portion 410. The second portion 420 defines a second portion of the passageway 430, which extends from the distal end 423 of the second portion 420 to the proximal end 421 of the second portion 420. The first portion 410 of the passageway 430 has a constricted cross-sectional area moving from the distal end 413 to the proximal end 411 of the first portion 410 to cause fluid, for example air, to accelerate through this first portion 410 of the inner longitudinal passageway 430 when negative pressure is applied at the proximal end 101 of the aerosol-generating article 100. The cross-sectional area of the first portion 410 of the inner longitudinal passageway 430 narrows from the distal end 413 to the proximal end 411 of the first portion 410. The second portion 420 of the inner longitudinal passageway 430 has an expanding cross-sectional area from the distal end 423 to the proximal end 421 of the second portion 420 of the fluid guide 400. In the second portion 420 of the inner longitudinal passageway 430, fluid may decelerate.

The wrapper 110 defines an open, proximal end 101 of the aerosol-generating article 100 and a distal end 103. A tubular element 600 comprising gel composition 500 is disposed in the distal end 103 of the aerosol-generating article 100. The aerosol-generating article 100 comprises an end plug at its extreme distal end 103. The end plug is positioned to the distal side of the tubular element 600. The end plug comprises material of a high resistance to draw hence biasing fluid to enter the aerosol-generating article 100 though the apertures 150 when a negative pressure is applied to the proximal end 101 of the aerosol-generating article 100. Aerosol generated or released from the tubular element 600 comprising nicotine, when heated may enter the cavity 140 in the aerosol-generating article downstream from the tubular element 600, to be carried through the inner longitudinal passageway 430.

Apertures 150 extend through the wrapper 110. At least one aperture 150 is in communication with an outer longitudinal passageway 440 formed between an outer surface of the fluid guide 400 and an inner surface of the wrapper 110. A seal is formed between the fluid guide 400 and the wrapper 110 at a location between the apertures 150 and the proximal end 101.

When a negative pressure is applied to the proximal end 101 of the aerosol-generating article 100, fluid enters the apertures 150, flows through the outer longitudinal passageways 440 into the cavity 140 and to the tubular element 600 comprising gel composition where the fluid may entrain aerosol when the tubular element 600 comprising gel composition, is heated. The fluid then flows through the inner longitudinal passageway 430, and through the proximal end 101 of the aerosol-generating article 100. As fluid flows through the first portion 410 of the inner longitudinal passageway 430, the fluid accelerates. As fluid flows through the second portion of the inner longitudinal passageway 430, the fluid decelerates. In the depicted embodiment, the wrapper 110 defines a proximal cavity 130 between proximal end 401 of the fluid guide 400 and the proximal end 101 of the article 100, which could serve to decelerate the fluid prior to exiting the mouth end 101.

EXAMPLES

Table 1 describes gel composition formulations that were formulated.

TABLE 1

| Example | Formulation (w/w) | Change in Shape at Ambient RH |
|---|---|---|
| 1 | 0.5% Low Acyl Gellan<br>0.5% Guar<br>2% Nicotine<br>0.5% Calcium<br>1.3% Levulinic acid<br>95.2% Glycerol | Yes |
| 2 | 0.5% Low Acyl Gellan<br>0.5% Guar<br>2% Nicotine<br>0.5% Calcium<br>1.3% Levulinic acid<br>85.2% Glycerol<br>10% Water | Yes |
| 3 | 1% Low Acyl Gellan<br>1% Agar<br>1% Xanthan<br>2% Nicotine<br>1% Calcium<br>1.3% Levulinic acid<br>92.7% Glycerol | Slight |
| 4 | 1% Low Acyl Gellan<br>1% Xanthan<br>1% Agar<br>2% Nicotine<br>0.5% Calcium<br>1.3% Levulinic acid<br>20% Water<br>72.7% Glycerol | No |
| 5 | 2% Low Acyl Gellan<br>1% Xanthan<br>2% Nicotine<br>0.5% Calcium<br>1.3% Levulinic acid<br>20% Water<br>72.7% Glycerol | No |
| 6 | 1.5% Low Acyl Gellan<br>1.5% High Acyl Gellan<br>2% Nicotine<br>1% Calcium | No |

TABLE 1-continued

| Example | Formulation (w/w) | Change in Shape at Ambient RH |
|---|---|---|
| 7 | 1.3% Levulinic acid<br>72.7% Glycerol<br>1% Alginate<br>1% Xanthan<br>1% Agar<br>2% Nicotine<br>1% Calcium<br>1.3% Levulinic acid<br>20% Water<br>72.7.2% Glycerol | No |
| 8 | 3% Low Acyl Gellan<br>2% Nicotine<br>1% Calcium<br>1.3% Levulinic acid<br>20% Water<br>72.7.2% Glycerol | No |
| 9 | 1% Agar<br>2% Nicotine<br>1.3% Levulinic acid<br>30% Water<br>65.7% Glycerol | — |

Indentation Test

Measurements were conducted using an Anton Parr PNR12 penetrometer and a quarter-cone plate. Samples (gel compositions) were loaded under the needle and aligned manually with the top of the sample surface. The tip of the needle's shadow on the sample was brought into contact with the needle. At least three measurements were conducted per sample. The mean distance penetrated for each gel was measured.

Example 1 had a distance penetrated of about 7.5 mm.
Example 2 had a distance penetrated of about 7.7 mm.
Example 3 had a distance penetrated of about 7.0 mm.
Example 4 had a distance penetrated of about 3.8 mm.
Example 9 had a distance penetrated of about 5.0 mm.

The greater the distance penetrated, the softer the gel composition.

Gel Composition Weight Change Over Time

The weights of several example formulations were evaluated over 45 days at various relative humidities. A stable gel composition will substantially maintain its initial weight over the 45 days.

Example 4 was weighed over 45 days at three relative humidity levels (10%, 60% and 70%). At 60% relative humidity, this gel composition added about 10% to its weight over the 45 days with nearly all of the weight gain occurring in the first 5 days. At 10% relative humidity, this gel composition lost about 15% to its weight over the 45 days with nearly all of the weight loss occurring in the first 5 days. At 70% relative humidity, this gel composition added about 25% to its weight over the 45 days with nearly all of the weight gain occurring in the first 5 days. At all three relative humidity levels (10%, 60% and 70%) no liquid phase was observed.

Example 2 was weighed over 45 days at three relative humidity levels (10%, 60% and 70%). At 60% relative humidity, this gel composition added about 15% to its weight over the 45 days with nearly all of the weight gain occurring in the first 5 days. At 10% relative humidity, this gel composition lost about 5% to its weight over the 45 days with nearly all of the weight loss occurring in the first 5 days. At 70% relative humidity, this gel composition added about 45% to its weight over the 45 days with nearly all of the weight gain occurring in the first 5 days.

Further Examples

Table 2 describes gel composition formulations that were formulated.

TABLE 2

| Example | Formulation (w/w) |
|---|---|
| 10 | 1% Low Acyl Gellan<br>1% Xanthan<br>1% Agar<br>2% Nicotine<br>0.5% Calcium<br>1.3% Lactic acid<br>20% Water<br>72.7% Glycerol |
| 11 | 1% Alginate<br>1% Xanthan<br>1% Agar<br>2% Nicotine<br>0.5% Calcium<br>1.3% Lactic acid<br>20% Water<br>72.7% Glycerol |
| 12 | 2% Low Acyl Gellan<br>1% Xanthan<br>2% Nicotine<br>0.5% Calcium<br>1.3% Lactic acid<br>20% Water<br>72.7% Glycerol |
| 13 | 1.5% Low Acyl Gellan<br>1.5% High Acyl Gellan<br>2% Nicotine<br>1% Calcium<br>1.3% Lactic acid<br>20% Water<br>72.7% Glycerol |
| 14 | 3% Low Acyl Gellan<br>2% Nicotine<br>1% Calcium<br>1.3% Lactic acid<br>20% Water<br>72.7% Glycerol |

The invention claimed is:

1. A gel composition, comprising:
   an alkaloid compound, or a cannabinoid compound, or both an alkaloid compound and a cannabinoid compound;
   at least 50% wt. glycerol;
   at least 0.2% wt. ionic crosslinking gelling agent;
   at least 0.2% wt. viscosifying agent or at least 0.2% wt. hydrogen-bond crosslinking gelling agent; and
   an acid.

2. The gel composition according to claim 1, wherein the alkaloid compound is nicotine.

3. The gel composition according to claim 2, comprising:
   about 0.5% to about 2.5% wt. nicotine;
   at least 70% wt. glycerol;
   at least 0.5% wt. hydrogen-bond crosslinking gelling agent;
   at least 0.5% wt. viscosifying agent;
   at least 0.5% wt. ionic crosslinking gelling agent;
   divalent ions; and
   an acid.

4. The gel composition according to claim 1, wherein the composition comprises about 0.5% to about 5% wt. acid.

5. The gel composition according to claim 1, wherein the acid comprises lactic acid.

6. The gel composition according to claim 1, wherein the acid comprises levulinic acid.

7. The gel composition according to claim 1, further comprising calcium ions.

8. The gel composition according to claim 1, wherein the viscosifying agent, hydrogen-bond crosslinking gelling, agent, and ionic crosslinking gelling agent are each present in the gel composition in about 0.5 to 2.5% wt.

9. The gel composition according to claim 2, comprising:
about 0.5% to about 2.5% wt. nicotine;
about 70% wt. to about 80% wt. glycerol;
about 0.5% to about 2% wt. viscosifying agent;
about 0.5% wt. to about 2% wt. hydrogen-bond crosslinking gelling agent;
about 0.5% wt. to about 2% wt. ionic crosslinking gelling agent;
about 0.5% wt. to about 2.5% wt. carboxylic acid;
divalent ions; and
about 15% wt. to about 25% wt. water.

10. The gel composition according to claim 1, wherein the viscosifying agent comprises xanthan gum.

11. The gel composition according to claim 1, wherein the hydrogen-bond crosslinking gelling agent comprises agar.

12. The gel composition according to claim 1, wherein the ionic crosslinking gelling agent comprises low acyl gellan.

13. The gel composition according to claim 2, comprising:
about 1.5% to about 2.5% wt. nicotine;
about 70% to about 75% wt. glycerol;
about 18% to about 22% wt. water;
about 0.5% to 2% agar;
about 0.5% to 2% xanthan gum;
about 0.5% to 2% low acyl gellan;
about 0.5% wt. to about 2.5% wt. carboxylic acid;
divalent ions; and
about 15% wt. to about 25% wt. water.

14. The gel composition according to claim 13, wherein the acid comprises lactic acid.

15. The gel composition according to claim 13, comprising calcium ions.

16. A method of generating a vapour comprising an alkaloid compound, or a cannabinoid compound, or both an alkaloid compound and a cannabinoid compound, the method comprising heating a gel composition according to claim 1 to vaporize the alkaloid compound, or the cannabinoid compound, or both the alkaloid compound and the cannabinoid compound.

* * * * *